United States Patent
Hao et al.

(10) Patent No.: US 9,993,414 B2
(45) Date of Patent: Jun. 12, 2018

(54) ORAL CARE COMPOSITION COMPRISING AN AMADORI COMPOUND

(71) Applicant: Colgate-Palmolive Company, Piscataway, NJ (US)

(72) Inventors: Zhigang Hao, Bridgewater, NJ (US); Ying Yang, South Brunswick, NJ (US); Zhiqiang Liu, Bridgewater, NJ (US); Katherine Hu, East Brunswick, NJ (US); Guofeng Xu, Plainsboro, NJ (US); Paul Joseph Vincenti, Jefferson, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

(21) Appl. No.: 14/652,785

(22) PCT Filed: Dec. 17, 2012

(86) PCT No.: PCT/US2012/070101
§ 371 (c)(1),
(2) Date: Jun. 16, 2015

(87) PCT Pub. No.: WO2014/098793
PCT Pub. Date: Jun. 26, 2014

(65) Prior Publication Data
US 2015/0328120 A1    Nov. 19, 2015

(51) Int. Cl.
*A61K 8/60* (2006.01)
*A61Q 11/00* (2006.01)
*A61K 8/44* (2006.01)

(52) U.S. Cl.
CPC .............. *A61K 8/60* (2013.01); *A61Q 11/00* (2013.01); *A61K 2800/92* (2013.01)

(58) Field of Classification Search
USPC .................... 424/49, 52, 48, 53, 58, 54
See application file for complete search history.

(56) References Cited

U.S. PATENT DOCUMENTS

| | | | |
|---|---|---|---|
| 4,251,548 A * | 2/1981 | Ogawa | A23G 4/06 426/3 |
| 5,541,341 A * | 7/1996 | Vermeer | C07D 207/408 548/112 |
| 5,776,435 A | 7/1998 | Gaffar et al. | |
| 7,939,306 B2 | 5/2011 | Szeles et al. | |
| 2006/0140881 A1 * | 6/2006 | Xu | A61K 8/345 424/49 |
| 2010/0022432 A1 | 1/2010 | Maurer et al. | |
| 2010/0330013 A1 | 12/2010 | O'Connell et al. | |

FOREIGN PATENT DOCUMENTS

| | | | |
|---|---|---|---|
| DE | 3439610 | | 4/1986 |
| DE | 102007054653 | | 5/2009 |
| GB | 1004774 | | 9/1965 |
| JP | 55-104858 | * | 8/1980 |
| JP | 09221667 | * | 8/1997 |

OTHER PUBLICATIONS

Amadori et al., "Products of condensation between glucose and phenitidine," Atti Accad. Naz. Lincei, 1925, 2(6):337-342.
Balls et al., "The Milk-Clotting action of papain," J. Biol. Chem., 1937, 121:737-745.
Davidek et al., "Degradation of the Amadori Compound N-(1-Deoxy-D-fructos-1-yl) glycine in Aqueous Model Systems," J. Agric. Food Chem. 2002, 50:5472-5479.
Mills et al., "Amadori Compounds as Nonvolatile Flavor Precursors in Processed Foods", Agric. Food Chem., Jul.-Aug. 1969, 17(4):723-727.
Mossine et al., "The preparation and characterization of some Amadori compounds (1-amino-1-deoxy-D-fructose derivatives) derived from a series of aliphatic ω-amino acids," Carbohyd. Res., Sep. 1994, 262(2):257-270.

* cited by examiner

*Primary Examiner* — Lezah Roberts

(57) ABSTRACT

The present invention relates to oral care compositions and methods of inhibiting microbial biofilm formation and/or degrading a microbial biofilm. Disclosed herein are oral care compositions comprising an Amadori compound having a glucose moiety and an amino acid moiety. The Amadori compound has use for inhibiting oral microbial biofilm formation and/or degrading an oral microbial biofilm in the oral cavity of a mammalian subject.

10 Claims, No Drawings

ORAL CARE COMPOSITION COMPRISING AN AMADORI COMPOUND

BACKGROUND OF THE INVENTION

A biofilm is a structured group of microorganisms encapsulated within a self-developed polymeric extracellular matrix. Biofilms are typically adhered to a living or inert surface. In the human or animal body biofilms can form on any internal or external surface. Biofilms have been found to be involved in a wide variety of microbial infections in the body and cause a number of conditions including urinary tract infections, middle-ear infections, and in particular, diseases of the oral cavity.

A plaque biofilm is a soft deposit that forms on dental surfaces, and provides a locus for calculus or tartar formation. As such, plaque biofilm is implicated in the occurrence of gingivitis, periodontitis, caries and other forms of periodontal disease. Plaque biofilm adheres firmly to dental surfaces and is removed only with difficulty even through a rigorous brushing regimen. Moreover, plaque biofilm rapidly reforms on the tooth surface after it is removed.

It is known that glucose can be metabolized in the oral cavity by the action of the enzymes generated from several oral bacterial components, such as S. mutans. The glucose can be polymerized into glucans in the mouth by the action of the enzymes, and such polymerization can cause biofilm formation on the tooth surface, which can subsequently form oral plaque the tooth surface.

There is a continuing need to provide oral care compositions which can reduce or prevent biofilm formation, with consequential reduction in the formation of oral plaque.

There is therefore the need to provide improved agents for use in oral care compositions which effectively inhibit biofilm formation and/or degrade biofilms.

SUMMARY OF THE INVENTION

The invention meets the needs in the art for reducing or preventing biofilm formation by administering Amadori products to the oral cavity.

Amadori compounds (also known as Amadori products) are formed via the well-known Amadori rearrangement reaction whereby a aldose sugar is isomerized via an acid or base and then reacted with an amine to form the Amadori compound after rearrangement of a Schiff base intermediate (see M. Amadori, *Atti Accad. Naz. Lincei* 2(6), 337 (1925); The Merck Index (14$^{th}$ Edition), pg. ONR-3, (2006)). The reaction scheme below shows the reaction between a hexose sugar and ammonia to form an Amadori compound.

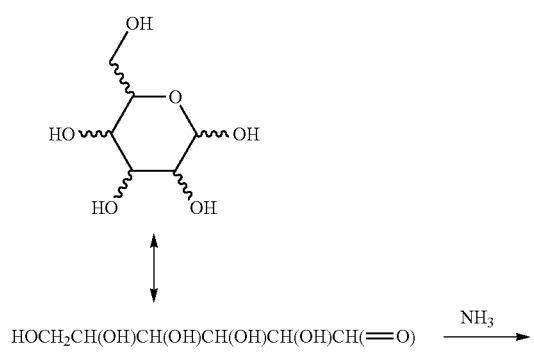

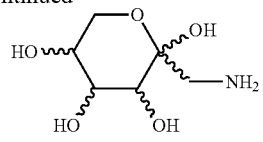

$HOCH_2CH(OH)CH(OH)CH(OH)C(=O)CH_2NH_2$

"Amadori compound"
from reaction of aldose (e.g. hexose) sugar with ammonia

Amadori rearrangements whereby the aldose sugar is reacted with an amino acid are also referred to as Maillard reactions.

Although the method for making Amadori compounds (products) is well known in the art, their usage is less known in the art. Amadori compounds are considered not have benefits by themselves, but to function as intermediate compounds for the formation of advanced glycosylation end products (AGEs) wherein the Amadori compound is oxidized. These AGEs often have benefit in the food industry as flavorants. One such example is the pyrolysis of Amadori compounds to produce compounds which have caramel odors. Mills et al., "Amadori Compounds as Nonvolatile Flavor Precursors in Processed Foods", *Agric. Food Chem.*, vol. 17, no. 4, pgs 723-727 (July-August 1969).

However, it has surprisingly been discovered that Amadori compounds are useful in their own right as agents to reduce or inhibit biofilm formation.

In a first aspect, the invention provides an oral care composition comprising an Amadori compound.

Optionally, the Amadori compound is formed by the reaction of a ketose sugar with an amino acid.

Optionally, the Amadori compound is formed by the reaction of glucose with an amino acid wherein the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine.

In a second aspect, the invention provides a composition is for treating or preventing dental plaque in the oral cavity of a mammalian subject.

In a third aspect, the invention provides an oral care composition comprising an Amadori compound having a glucose moiety and an amino acid moiety for inhibiting oral microbial biofilm formation and/or degrading oral microbial biofilm.

In a fourth aspect, the invention provides a method of inhibiting oral microbial biofilm formation and/or degrading an oral microbial biofilm in the oral cavity of a mammalian subject comprising administering to the subject a composition comprising an Amadori compound having a glucose moiety and an amino acid moiety.

In a fifth aspect, the invention provides the use of an Amadori compound having, in an oral care composition, for inhibiting oral microbial biofilm formation and/or degrading an oral microbial biofilm in the oral cavity of a mammalian subject. The invention is based upon the finding of the inventors that Amadori compounds exhibit good oral health benefits, and in particular can provide reduced biofilm and plaque formation in oral care compositions.

Further embodiments of the invention will be apparent from the detailed description and the examples.

DESCRIPTION OF THE INVENTION

It should be understood that the detailed description and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

Optionally, the Amadori compound is formed by the reaction of glucose with an amino acid wherein the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. Open chain and ring forms of the Amadori compound formed from the reaction of a D-glucose with an amino acid is shown on the next page for illustrative purposes only; L-forms of glucose are also considered to be within the scope of this invention.

Amadori compound from reaction product of D-glucose and an amino acid

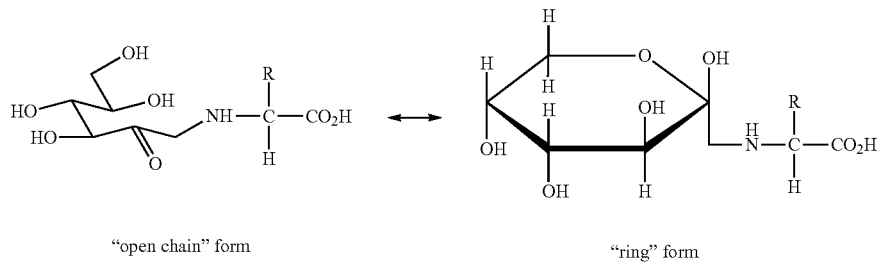

"open chain" form          "ring" form

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

In some embodiments, the invention provides an oral care composition comprising an Amadori compound including a glucose moiety and an amino acid moiety. In particular embodiments, the composition is for treating or preventing dental plaque in the oral cavity of a mammalian subject. In particular embodiments, the Amadori compound is an oral microbial biofilm reducing or preventing agent in the composition. In particular embodiments, the oral care composition comprises an Amadori compound having a glucose moiety and an amino acid moiety for inhibiting oral microbial biofilm formation and/or degrading oral microbial biofilm.

Amadori Compound

In a first aspect, the invention provides an oral care composition comprising an Amadori compound.

Optionally, the Amadori compound is formed by the reaction of an aldose sugar with an amine compound.

Optionally, the Amadori compound is formed by the reaction of a pentose or hexose sugar with an amino acid compound.

R is a side chain for alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine. For proline, the R side chain and the nitrogen form a pyrrolidine ring.

The above structure of the Amadori compounds described in this application are also intended to encompass salt forms and charged forms thereof. In addition, although the above Amadori compound depicts a D-glucose, Amadori compounds from L-glucose are also considered to be part of the invention.

The Amadori compounds formed by the reaction of glucose and glycine can also be represented as N-(1-deoxy-fructos-1-yl)glycine. Similarly, the reaction of glucose with other naturally occurring amino acids can be represented as:
N-(1-deoxy-fructos-1-yl)alanine;
N-(1-deoxy-fructos-1-yl)arginine;
N-(1-deoxy-fructos-1-yl)asparagine;
N-(1-deoxy-fructos-1-yl)aspartic acid;
N-(1-deoxy-fructos-1-yl)cysteine;
N-(1-deoxy-fructos-1-yl)glutamine;
N-(1-deoxy-fructos-1-yl)glutamic acid;
N-(1-deoxy-fructos-1-yl)glycine;
N-(1-deoxy-fructos-1-yl)histidine;
N-(1-deoxy-fructos-1-yl)isoleucine;
N-(1-deoxy-fructos-1-yl)leucine;
N-(1-deoxy-fructos-1-yl)lysine;
N-(1-deoxy-fructos-1-yl)methionine;
N-(1-deoxy-fructos-1-yl)phenylalanine;
N-(1-deoxy-fructos-1-yl)serine;
N-(1-deoxy-fructos-1-yl)threonine;
N-(1-deoxy-fructos-1-yl)tryptophan;
N-(1-deoxy-fructos-1-yl)tyrosine; and
N-(1-deoxy-fructos-1-yl)valine.

Both the D- and L-forms and open chain and claims

Optionally, the amino acid is selected from the group consisting of glycine, lysine, glutamic acid and arginine. Further optionally, the amino acid moiety is glycine or glutamic acid. Still further optionally, the amino acid moiety is glycine.

Optionally, the Amadori compound is present in the composition at a concentration of from about 0.005 wt % to about 10 wt % based on the total weight of the composition, further optionally from about 0.1 wt % to about 7.5 wt % based on the total weight of the composition, still further optionally from about 1 wt % to about 5 wt % based on the total weight of the composition.

In one embodiment of the invention, the amino acid may be selected from the group consisting of glycine, lysine, glutamic acid and arginine (N-(1-deoxy-fructos-1-yl)glycine; N-(1-deoxy-fructos-1-yl)lysine; N-(1-deoxy-fructos-1-yl)glutamic acid; N-(1-deoxy-fructos-1-yl)arginine).

In some embodiments, the amino acid moiety is glycine or glutamic acid, preferably glycine.

Biofilm

The term "biofilm" used in the context of the invention means any group of microorganisms encapsulated within a self-developed polymeric extracellular matrix. The biofilm may be adhered to a living or inert surface. For example, in the oral cavity, the biofilm may be adhered to teeth in the form of plaque.

The biofilm may be formed from one or more different types of microorganisms including for example bacteria, archaea, protozoa, fungi and algae. The biofilm is preferably formed from bacteria. In one embodiment the biofilm is formed from a single species of bacteria. In another embodiment, the biofilm is formed from a plurality of species of bacteria. The biofilm may be formed from one or more bacteria selected from *Actinomyces viscosus, Lactobacillus casei, Streptococcus oralis, Fusobacterium nucleatum, Veillonella parvula* and *Porphyromonas gingivalis.*

Optional Agents for Oral Care Composition

The composition according to the invention may also comprise one or more further agent(s) which is or are operably for the prevention or treatment of a condition or a disorder of hard or soft tissue of the oral cavity, the prevention or treatment of a physiological disorder or condition, or which provide(s) a cosmetic benefit.

The further agents are typically selected from an antimicrobial agent (which is not an Amadori compound), antiplaque agent, a whitening agent, cleaning agent, a flavoring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agents, an anti-sensitivity agent, an antioxidant agent, nutrients, enzymes and combinations thereof. It is understood that while general attributes of each of the above categories of materials may differ, there may be some common attributes, and any given material may serve multiple purposes within two or more of such categories of materials. Preferably, the carrier is selected for compatibility with other ingredients of the composition.

In some embodiments, the compositions of the invention optionally comprise an antimicrobial (e.g., antibacterial) agent. The antimicrobial agent may be selected from Triclosan, cetyl pyridinium chloride, magnolia extract, magnolol, honokiol, butyl magnolol, propyl honokiol, zinc chloride, zinc lactate, zinc citrate, stannous fluoride and stannous chloride. A further illustrative list of useful antibacterial agents is provided in U.S. Pat. No. 5,776,435 (Gaffar et al.), the contents of which are incorporated herein by reference.

One or more antimicrobial agents are optionally present in amount effective to inhibit and/or degrade a biofilm in the oral cavity. Preferably, the antimicrobial agent is present in an amount suitable to prevent or treat a condition caused by biofilm formation, such as a condition selected from dental plaque, tooth decay, periodontal disease, gingivitis or halitosis.

Typically the antimicrobial agent is present in the composition at a concentration of about 0.001 wt % to about 10 wt %, for example about 0.1 wt % to about 3 wt %, each based on the total weight of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01 wt % to about 5 wt %, optionally in various embodiments from about 0.05 to about 2 wt %, from about 0.1 wt % to about 2.5 wt %, and from about 0.1 to about 0.5 wt %.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, flakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001 wt % to about 20 wt %, for example about 0.01 wt % to about 10 wt % or about 0.1 wt % to about 5 wt %.

The compositions of the invention may further comprise an optional abrasive useful for example as a polishing agent. Some embodiments provide oral care compositions comprising from about 5 to about 15 wt % abrasive based on the total weight of the composition.

When abrasives are present, the average particle size is generally about 0.1 to about 30 microns, for example about 1 to about 20 or about 5 to 15 microns.

Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), poly-olefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

Fluoride salts and fluoride ion sources, e.g., fluoride salts which may be soluble, are known in the art and may be incorporated into the compositions of the invention. Representative fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt % to about 10 wt %, e.g., from about 0.003 wt % to about 5 wt %, 0.01 wt % to about 1 wt, or about 0.05 wt %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions of the invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the invention optionally incorporate one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt % to about 20 wt % by weight based on the total weight of the composition, depending on the agent chosen. The compositions of the invention may also be used to treat hypersensitivity by blocking dentin tubules when applied to a tooth.

The compositions of the invention may also include a tooth whitening or tooth bleaching composition, which are known in the art. Suitable whitening and bleaching composition include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1 wt % to about 20 wt % by weight based on the total weight of the composition, depending on the agent chosen.

In some embodiments, the compositions of the invention further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In some embodiments, the compositions of the invention further comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

The compositions of the invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

The enzymes useful in the practice of the present invention are described in U.S. Pat. No. 7,939,306 which is incorporated by reference. These enzymes include protein substances within the class of proteases, which breakdown or hydrolyze proteins (proteases). These proteolytic enzymes are obtained from natural sources or by the action of microorganisms having a nitrogen source and a carbon source. Examples of proteolylic enzymes useful in the practice of the present invention include papain, bromelain, chymotrypsin, ficin and alcalase.

Papain obtained from the milky latex of the Papaya tree is the proteolytic enzyme preferred for use in the practice of the present invention and is incorporated in the oral care composition of the present invention in an amount of about 0.1 to about 10% by weight and preferably about 0.5 to about 5% by weight, such papain having an activity of 150 to 300 MCU per milligram as determined by the Milk Clot Assay Test of the Biddle Sawyer Group (see J. Biol. Chem., vol. 121, pages 737-745).

An additional enzyme which is formulated in combination with the protease enzyme papain is glucoamylase. Glucoamylase is a saccharifying glucoamylase of Aspergillus niger origin cultivated by fermentation. This enzyme can hydrolyze both the alpha-D-1,6 glucosidic branch points and the alpha-1,4 glucosidic bonds of glucosyl oligosaccharides. The product of this invention comprises about 0.001 to 2% of the carbohydrase and preferably about 0.01 to 0.55% by weight. Additional carbohydrases useful in accordance with this invention are glucoamylase, alpha and beta-amylase, dextranase and mutanase.

Other enzymes which may be used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

The lipase enzyme is derived from a select strain of Aspergillus niger, exhibiting random cleaving of the 1,3 positions of fats and oils. The enzyme has maximum lipolytic activity at pH 5.0 to 7.0 when assayed with olive oil. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from Aspergillus niger and Aspergillus allianceus and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmurarnic acid and carbon number 4 of N-acetyl-D-glucosamine, which in vivo, are polymerized to form the cell wall polysaccharide. Additionally, pectinase, an enzyme that is present in most plants, facilitates the hydrolysis of the polysaccharide pectin into sugars and galacturonic acid.

In various embodiments, the oral composition according to the invention is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), the oral composition is intentionally swallowed, optionally after retention in the oral cavity for a time sufficient to effect intended utility.

The composition according to the invention preferably comprises an orally acceptable carrier in a product such as dentifrice, mouthwash, mouthrinse, toothpaste, gel, dental cream, chewing gum, or portable dosage article such as, without limitation, a lozenge, a mint, bead, wafer, liquid formulated for oral application in a small portable nebulizer (spray bottle), liquid formulated for oral application in a small portable drop-generating bottle, or a soft pliable tablet ("chewie"). If used in animals or pets, veterinary pastes, chewables or treats may also be used as the orally acceptable carrier.

As used herein, an "orally acceptable carrier" refers to a material or combination of materials that are safe for use in the compositions of the invention, commensurate with a reasonable benefit/risk ratio.

In some embodiments, the invention also provides a portable dose article comprising an oral care composition as defined above, wherein the portable dose article is selected from a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

All of the ingredients in the compositions may have functions in addition to their primary function, and may contribute to the overall properties of the composition, including stability, efficacy, consistency, mouthfeel, taste, odor and so forth.

Methods of Use

The composition according to the invention may be administered to or applied to a human or other mammalian subject. The composition may be suitable for administration or application to the oral cavity of a human or mammalian subject. Typically, the composition is for inhibiting microbial biofilm formation and/or degrading microbial biofilm.

In some embodiments, the invention provides a method of inhibiting oral microbial biofilm formation and/or degrading an oral microbial biofilm in the oral cavity of a mammalian subject comprising administering to the subject a composition comprising an Amadori compound.

In some embodiments, the method comprises treating or preventing dental plaque in the oral cavity of a mammalian subject.

In some embodiments, the invention provides the use of an Amadori compound, in an oral care composition, for inhibiting oral microbial biofilm formation and/or degrading an oral microbial biofilm in the oral cavity of a mammalian subject.

In some embodiments, the invention further provides a composition as defined above for preventing or treating a disease condition of the oral cavity. Typically, the disease condition is caused by biofilm formation. The disease condition may be selected from dental plaque, tooth decay, periodontal disease, gingivitis and halitosis.

Accordingly, the invention provides a composition as defined above for use as a medicament, and in particular, for use in inhibiting microbial biofilm formation and/or degrading microbial biofilm.

A medicament comprising the composition according to the invention may be administered to a patient. The carbohydrate antimetabolite may effectively inhibit biofilm formation and/or degrade a biofilm without being incompatible or unstable with other oral care active ingredients and without inactivating other desirable additional oral care ingredients, whilst easily delivered in vivo.

The invention is illustrated in the following non-limiting examples.

EXAMPLES

Example 1

In this example, an Amadori compound from the reaction of glucose with glycine was prepared (N-(1-deoxy-fructos-1-yl)glycine).

A mixture of 50 grams of D-glucose (278 mmol), 8 grams of sodium pyrosulphite ($Na_2S_2O_5$, 42 mmol) and 7.5 mL of deionized (DI) water was heated to 95° C. Then 5 grams of glycine (66 mmol) was added to the mixture and the resultant mixture was heated at 95° C. for 1 hour. The orange-brown reaction mixture was diluted with EtOH to a final volume of 360 mL containing 61 wt % EtOH. Two further batches of the reaction mixture were prepared in the same manner.

A chromatography column incorporating a resin (Dowex® HCR-W2, hydrogen form) was provided. The column had 200 gram of resin and a column size for the resin of 4 cm internal diameter×18 cm length, and a total column length of 60 cm. The resin was preconditioned with 800 mL of 2 N HCl followed by 450 mL of 1 N NaOH, 800 mL of 1 N HCl and 200 mL of DI water. About 700 mL of the reaction mixture was loaded into the resin column. The column separation was performed with 400 mL of EtOH (70 vol. %), 500 mL of DI water, and 1000 mL of ammonia solution (0.22 N). The resulting extract was divided into plural successive 100mL fractions. Each 100 mL fraction was checked for Amadori compound from the reaction of glucose with glycine using mass spectrometry. The mass spectrometer was set up with the MS detector at m/z: 238 [M+1].

The Amadori compound from the reaction of glucose with glycine was found to be present in the fraction is which eluted after 300 mL of the ammonia solution was applied. The fractions containing Amadori compound from the reaction of glucose with glycine were pooled and freeze dried. The resulting powder was dissolved in MeOH followed by crystallization to form crystallized Amadori compound from the reaction of glucose with glycine.

Example 2

In this example, an Amadori compound from the reaction of glucose with arginine was prepared (N-(1-deoxy-fructos-1-yl) arginine).

A mixture of 50 g of D-glucose (278 mmol), 8 g of sodium pyrosulphite ($Na_2S_2O_5$, 45 mmol), and 7.5 mL DI water was heated to 95° C. Then, 11.6 g of arginine was added to the mixture and the resultant mixture was heated at 95° C. for 1 hour. The orange-brown reaction mixture was diluted with 150 mL DI water and 220 mL of EtOH to a final volume of 370 mL.

The same resin column as used in Example 1 was employed to separate out the Amadori compound from the reaction of glucose with arginine. The resin was pre-conditioned with 400 mL of 2 N HCl followed by 225 mL of 1 N NaOH and then 400 mL of 1 N HCl. Subsequently, 200 mL of the sample solution was loaded into the resin column. The elution was performed with 400 mL of EtOH (70 vol. %), 400 mL of DI water and ammonia solution (0.22 N). Each 100 mL of fraction was checked for Amadori compound from the reaction of glucose with arginine using liquid chromatography/mass spectrometry (LC/MS). The fractions containing Amadori compound from the reaction of glucose with arginine were pooled and freeze dried. The resulting powder was dissolved in MeOH followed by recrystallization to form crystallized Amadori compound from the reaction of glucose with arginine.

Example 3

In this example, an Amadori compound from the reaction of glucose with lysine (N-(1-deoxy-fructos-1-yl)lysine).

A mixture of 50 g of D-glucose (278 mmol), 8 g of sodium pyrosulfite ($Na_2S_2O_5$, 45 mmol), and 7.5 mL DI water was heated to 95° C. Then 12.2 g of lysine was added to the mixture and the resultant mixture was heated at 95° C. for 1 hour. The orange-brown reaction mixture was diluted with 150 mL DI water and 220 mL of EtOH to a final volume of 370 mL.

The same resin column as used in Example 1 was employed to separate out Amadori compound from the reaction of glucose with lysine. The resin was pre-conditioned with 400 mL of 2 N HCl followed by 225 mL of 1 N NaOH and then 400 mL of 1 N HCl. Subsequently, 200 mL of the sample solution was loaded into the resin column. The column separation was performed with 400 mL of EtOH (70 vol. %), 400 mL of DI water and ammonia solution (0.22 N). Each 100 mL of fraction was checked for Amadori compound from the reaction of glucose with lysine using LC/MS. The fractions containing Amadori compound from the reaction of glucose with lysine were pooled and freeze dried. The resulting powder was dissolved in MeOH followed by recrystallization to form crystallized Amadori compound from the reaction of glucose with lysine.

Example 4

In this Example, Amadori compound from the reaction of glucose with glutamic acid (N-(1-deoxy-fructos-1-yl)glutamic acid).

A solution of 3.74 g of potassium hydroxide (67 mmol) in anhydrous methanol (100 mL) was added to 9.82 g of L-glutamic acid (67 mmol) and stirred until the amino acid was somewhat dissolved. Methanol (300 mL) and 7.2 g of D-glucose (40 mmol) were added, and the suspension was stirred and heated under reflux for 1 hour at 75° C. The methanol that was boiled off and collected was replaced, and the mixture was again heated under reflux for 1 hour at 75° C. For a second time, the methanol that was boiled off and collected was replaced. Another 3.7408 g of potassium hydroxide (67 mmol) was added to the mixture before heating under reflux for 1 hour at 75° C.

The resulting orange-brown reaction mixture was cooled to ambient temperature and concentrated to 100 mL under vacuum. The surplus of amino acid was removed by filtration and the filtrate containing the product was transferred to four centrifuge vials. Acetone was added dropwise to the filtrate, and the resulting yellow precipitate in excess acetone was centrifuged for 15 min at 9000 rpm. The supernatant liquid was removed and 20 mL of methanol was added to re-dissolve the resultant solid pellet. The sample was purified by a 2-fold recrystallization from methanol/acetone to form crystallized Amadori compound from the reaction of glucose with glutamic acid.

Example 5

In this Example, the ability of Amadori compound from the reaction of glucose with glycine to inhibit glucose metabolism with *Streptococcus mutans* was investigated.

Glucose usually can be metabolized in the mouth by the enzymes generated from several oral bacterial components, such as *S. mutans*, which can be present in the oral cavity.

A stock glucose solution of 0.4 wt % glucose dissolved in distilled water (0.4 g/100 mL) was prepared. A stock Amadori compound from the reaction of glucose with glycine solution of 4.0 wt % Amadori compound from the reaction of glucose with glycine dissolved in distilled water (0.4 g/10 mL) was prepared.

A bacterial solution was prepared as follows: *S. mutans* (ATCC #25175) was cultured overnight in TSB medium and then the resultant bacterial pellet was re-suspended bacterial to OD610=0.8 (a concentration with an optical reading of 0.8 at 610 nm for a 1-cm light path) with phosphate buffered saline (pH=7.4) (PBS).

In accordance with Example 5, a test sample comprising 1 mL of the bacterial solution, 0.5 mL of the Amadori compound from the reaction of glucose with glycine solution and 0.5 mL of the glucose solution was subjected to incubation at a temperature of 37° C., representing normal human body temperature.

Then, 200 μL of the test sample was transferred into individual HPLC vials after 10 minutes of the incubation period, after 30 minutes of the incubation period, and after 60 minutes of the incubation period. The HPLC vial cap was used to seal the vial. Immediately the HPLC vials were placed in a 100° C. water bath for about 5 minutes to denaturize the enzymes.

The resultant products were subjected to gas chromatography-mass spectrometry (GC-MS) testing and analysis to determine the amounts of the α- and β-glucose forms present. The results are shown in Table 1. In Table 1, the number of counts during MS detection for each respective α- and β-glucose form detected in the respective sample at the respective incubation time is indicated, the number of counts representing the amount of the respective glucose form present.

TABLE 1

| Incubation Time | Compounds | Comparative Example 1 | Example 5 | Glucose inhibition (%) from Example 5 |
|---|---|---|---|---|
| 10 minutes | α-glucose | 736391 | 1753564 | |
| | β-glucose | 1692159 | 3811348 | |
| | Total | 2428550 | 5564912 | 56.4 |
| 30 minutes | α-glucose | 782588 | 1912144 | |
| | β-glucose | 1710023 | 4308736 | |
| | Total | 2492611 | 6220880 | 59.9 |
| 60 minutes | α-glucose | 516114 | 1724203 | |
| | β-glucose | 1100953 | 3679788 | |
| | Total | 1617067 | 5403991 | 70.1 |

Comparative Example 1

In Comparative Example 1, the testing of Example 5 was repeated but on a control sample comprising 1 mL of the bacterial solution, 0.5 mL of the glucose solution and 0.5 mL of deionized water. In other words, Comparative Example 1 had no Amadori compound from the reaction of glucose with glycine. The control sample was also subjected to incubation at a temperature of 37° C. for the same respective time periods. The corresponding results are also shown in Table 1.

It may be seen from Table 1 that, comparing the test sample of Example 5 and the control sample of Comparative Example 1, the presence of Amadori compound from the reaction of glucose with glycine inhibits glucose metabolization in the presence of oral bacteria. In Example 5 when the Amadori compound from the reaction of glucose with glycine was present with glucose and the *S. mutans* bacterium, the glucose counts were high whereas in Comparative Example 1 when instead the Amadori compound from the reaction of glucose with glycine was not present with glucose and the *S. mutans* bacterium, the glucose counts were low. Accordingly, the Amadori compound from the reaction of glucose with glycine inhibited glucose metabolization.

When *S. mutans* is incubated with glucose at 37° C., glucose can be metabolized. However, when Amadori compound from the reaction of glucose with glycine was co-incubated with *S. mutans* and glucose, the results in Table 1 indicate that the glucose metabolism was significantly inhibited, i.e. at least 56% within the incubation time period of from 10 to 60 minutes.

Example 6

In this Example, the ability of Amadori compound from the reaction of glucose with glycine to inhibit biofilm formation was investigated.

A sample of cultured *S. mutans* (ATCC #25175) bacterium was grown in TSB medium overnight and subsequently centrifuged to form a pellet, and then the centrifuged *S. mutans* was re-suspended with TSB (trypticase soy broth) containing 1% glucose and adjusted to OD610=0.5 (a concentration with an optical reading of 0.5 at 610 nm for a 1-cm light path). A 50 microliter sample of the re-suspended *S. mutans* (OD610=0.5) was co-incubated with a 50 microliter test sample. The test sample contained 1 wt % of glucose and 2 wt % of Amadori compound from the reaction of glucose with glycine. The 100 μL total of the re-suspended *S. mutans* (OD610=0.5) and test sample, representing a clarified saliva, was co-incubated in a 96-well plate which was pre-coated with the clarified saliva and then left overnight at 37° C.

After the co-incubation period, the supernatant liquid was aspirated from the well plate. A 50 microliter amount of crystal violet was added to each well and permitted to stain any biofilm for a period of 10 minutes. The well plate was washed with 100 μL of PBS.

The amount of biofilm was determined by irradiating the well plate with electromagnetic radiation having a wavelength of 590 nm and measuring the absorbance. The results are given in Table 2. The lower the absorbance reading, the less the amount of biofilm detected.

Comparative Example 2

In Comparative Example 2, a control sample contained *S. mutans* and 1 wt % of glucose and was treated to the same co-incubation test and absorbance measurement as in Example 6. The results are shown in Table 2.

Example 7

In this Example, the ability of Amadori compound from the reaction of glucose with arginine to inhibit biofilm formation was investigated. The sample preparation and testing for biofilm were the same as that for Example 6 but instead of 1 wt % of glucose and 2 wt % of Amadori compound from the reaction of glucose with glycine, the test sample contained 1 wt % of glucose and 2 wt % of Amadori compound from the reaction of glucose with arginine. After the same co-incubation test the amount of biofilm was again determined using the test method of Example 6. The absorbance reading results are given in Table 2.

Example 8

In this Example, the ability of Amadori compound from the reaction of glucose with glutamic acid to inhibit biofilm formation was investigated.

The sample preparation and testing for biofilm were the same as that for Example 6 but instead of 1 wt % of glucose and 2 wt % of Amadori compound from the reaction of glucose with glycine, the test sample contained 1 wt % of glucose and 2 wt % of Amadori compound from the reaction of glucose with glutamic acid.

After the same co-incubation test the amount of biofilm was again determined using the test method of Example 6. The absorbance reading results are given in Table 2.

TABLE 2

|  | Example 6 | Example 7 | Example 8 | Comparative Example 2 |
| --- | --- | --- | --- | --- |
| Average absorbance (590 nm) | 0.2885 | 1.2808 | 0.5476 | 2.0346 |

Table 2 shows that Example 6 exhibited a low amount of biofilm, reflected by an average absorbance reading of 0.2885.

Table 2 shows that Example 7 also exhibited a reasonably low amount of biofilm, reflected by an average absorbance reading of 1.2808.

Table 2 shows that Example 8 also exhibited a low amount of biofilm, reflected by an average absorbance reading of 0.5476.

Table 2 shows that Comparative Example 2 exhibited a high amount of biofilm, reflected by an average absorbance reading of 2.0346.

Discussing the results of Examples 6 to 8 and Comparative Example 1, glucose usually can be polymerized into glucans in mouth by the action of the enzyme generated from several oral bacterial components, such as *S. mutans*. Such polymerization can cause biofilm formation on the tooth surface, which can subsequently form plaque. Experimentally, it was found from Examples 6 to 8 that when glucose was co-incubated with *S. mutans* and the respective Amadori compounds in the saliva coated 96-wellplate, the biofilm was inhibited as compared to when glucose was co-incubated with *S. mutans* without any Amadori compound in the saliva coated 96-wellplate. This experimental data shows that the Amadori compound inhibits biofilm formation, and consequently reduces plaque formation, on the surfaces of the teeth.

The biofilm formation results differ between the different Amadori compounds. As is shown in Table 2, both Amadori compound from the reaction of glucose with glycine and Amadori compound from the reaction of glucose with glutamic acid exhibited a very strong inhibition against biofilm formation whereas Amadori compound from the reaction of glucose with arginine exhibited relatively weak inhibition, which was nevertheless stronger than in the absence of Amadori compound from the reaction of glucose with arginine. It is believed by the inventors, without being bound by any theory, that the amino acid moiety side and electronic charge may affect the enzyme activity for the formation of glucans and therefore biofilm.

It is also believed by the inventors, without being bound by any theory, that the Amadori compounds, being similar in chemical structure to glucose, which can be attached on the enzyme active moiety during both glucose degradation and polymerization. However, since Amadori compounds are not glucose, they can effectively inhibit both glucose degradation and polymerization enzymes.

In summary, experimentally, it has been found that Amadori compound from the reaction of glucose with glycine can significantly inhibit glucose degradation and biofilm formation. Experimentally, it has been found that Amadori compound from the reaction of glucose with glutamic acid can also inhibit biofilm formation. Experimentally, it has further been found that, to a lesser extent, Amadori compound from the reaction of glucose with arginine can also inhibit biofilm formation.

The inventors therefore have found a new use of several Amadori compounds for oral care applications, e.g. four Amadori compounds representing the reaction product of glucose and an amino acid moiety selected from glycine (the smallest amino acid), glutamic acid (a negatively charged amino acid), lysine and arginine (a positively-charged amino acid) have been found significantly to inhibit glucose degradation to acids and biofilm formation with oral bacteria.

As those skilled in the art will appreciate, numerous changes and modifications may be made to the embodiments described herein without departing from the spirit of the invention. It is intended that all such variations fall within the scope of the appended claims.

The invention claimed is:

1. An oral care composition for inhibiting or reducing oral microbial biofilm formation and/or degrading an oral microbial biofilm in the oral cavity of a mammalian subject comprising an Amadori compound wherein the Amadori compound is a reaction product of a pentose or hexose sugar with an amino acid compound, wherein the Amadori compound is present in the composition at a concentration of from about 1 wt % to about 5 wt % based on the total weight of the composition, and wherein the composition comprises an orally acceptable carrier and is formulated as a dentifrice, a toothpaste, a gel, a dental cream, a mouthwash, a mouthrinse, a lozenge or a chewing gum.

2. The composition of claim 1, wherein the Amadori compound is a reaction product of glucose with an amino acid wherein the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

3. The composition of claim 2, wherein the amino acid is selected from the group consisting of glycine, lysine, glutamic acid and arginine.

4. The composition of claim 1, wherein the composition further comprises an antimicrobial agent (which is not an Amadori compound), anti-plaque agent, a whitening agent, cleaning agent, a flavoring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agents, an anti-sensitivity agent, an antioxidant agent, nutrients, enzymes and combinations thereof.

5. The composition of claim 4, wherein the antimicrobial agent is selected from the group consisting of Triclosan, cetyl pyridinium chloride, magnolia extract, magnolol, honokiol, butyl magnolol, propyl honokiol, zinc chloride, zinc lactate, zinc citrate, stannous fluoride and stannous chloride.

6. The composition of claim 4, wherein the tartar control agent is a polycarboxylate polymers or a polyvinyl methyl ether/maleic anhydride (PVM/MA) copolymers.

7. The composition of claim 4, wherein the enzyme is one or more enzymes selected from the group consisting of protease, carbohydrase, lipase, tannase, lysozyme, pectinase and combinations thereof.

8. The composition of claim 7, wherein the protease is selected from the group consisting of papain, bromelain, chymotrypsin, ficin, alcalase and combinations thereof and the carbohydrase is selected from the group consisting of glucoamylase, alpha-amylase, beta-amylase, dextranase, mutanase and combinations thereof.

9. A method of inhibiting oral microbial biofilm formation and/or degrading an oral microbial biofilm in the oral cavity of a mammalian subject comprising administering to the subject an oral care composition of claim 1.

10. The composition of claim 1, wherein the composition is formulated as a dentifrice, a toothpaste, a gel, a dental cream, a mouthwash, a mouthrinse, or a lozenge.

* * * * *